United States Patent
Martin et al.

(10) Patent No.: US 10,420,807 B2
(45) Date of Patent: Sep. 24, 2019

(54) LACTOBACILLUS SALIVARIUS FOR THE TREATMENT OF MASTITIS

(71) Applicant: N.V. Nutricia, Zoetermeer (NL)

(72) Inventors: Rocio Martin, Wageningen (NL); Jan Knol, Utrecht (NL); Leonides Fernández Álvarez, Madrid (ES); Irene Espinosa Martos, Madrid (ES); Esther Antonia Jiménez Quintana, Pozuelo de Alarcón (ES); Juan Miguel Rodríguez Gómez, Colmenar Viejo Madrid (ES)

(73) Assignee: N.V. NUTRICIA, Zoetermeer (NL)

( * ) Notice: Subject to any disclaimer, the term of this patent is extended or adjusted under 35 U.S.C. 154(b) by 362 days.

(21) Appl. No.: 15/105,774

(22) PCT Filed: Dec. 19, 2014

(86) PCT No.: PCT/NL2014/050890
§ 371 (c)(1),
(2) Date: Jun. 17, 2016

(87) PCT Pub. No.: WO2015/093963
PCT Pub. Date: Jun. 25, 2015

(65) Prior Publication Data
US 2017/0027997 A1  Feb. 2, 2017

(30) Foreign Application Priority Data
Dec. 19, 2013 (WO) ................ PCT/NL2013/050924

(51) Int. Cl.
| | |
|---|---|
| *A61K 9/19* | (2006.01) |
| *A61K 45/06* | (2006.01) |
| *C12N 1/20* | (2006.01) |
| *A61K 35/747* | (2015.01) |
| *C12R 1/225* | (2006.01) |

(52) U.S. Cl.
CPC .............. *A61K 35/747* (2013.01); *A61K 9/19* (2013.01); *A61K 45/06* (2013.01); *C12N 1/20* (2013.01); *C12R 1/225* (2013.01)

(58) Field of Classification Search
None
See application file for complete search history.

(56) References Cited

U.S. PATENT DOCUMENTS

2004/0057943 A1* 3/2004 Xaus Pey ............ A23C 9/1232
424/93.45

FOREIGN PATENT DOCUMENTS

WO    WO-2004/003235 A2    1/2004

OTHER PUBLICATIONS

Arroyo et al. 2010. Clinical Infectious Diseases, vol. 50, pp. 1551-1558., 2010.*
Arroyo et al., "Treatment of infectious mastitis during lactation: antibiotics versus oral administration of lactobacilli isolated from breast milk", Clinical Infectious Diseases, Jun. 2010, vol. 50, pp. 1551-1558.
Jimenez et al., "Oral administration of Lactobacillus strains isolated from breast milk as an alternative for the treatment of infectious mastitis during lactation", Applied and Environmental Microbiology, Aug. 2008, vol. 74, No. 15, pp. 4650-4655.
Leonides Fernandez et al., "The human milk microbiota: Origin and potential roles in health and disease", Pharmacological Research, 2013, vol. 69, pp. 1-10.
Martin et al., Lactobacillus salivirus CECT 5713, a potential probiotic strain isolated from infant feces and breast milk of a mother-child pair International Journal of Food Microbiology, 2006, vol. 112, pp. 35-43.
International Search Report issued in International Patent Application No. PCT/NL2014/050890, dated Feb. 24, 2015.

* cited by examiner

*Primary Examiner* — Padmavathi Baskar
(74) *Attorney, Agent, or Firm* — Gilberto M. Villacorta; Sunit Talapatra; Foley & Lardner LLP (57) ABSTRACT

The invention relates to a new strain of *Lactobacillus salivarius*, products containing the new strain, the use thereof in and methods for the treatment and/or prevention of inflammation and/or infection in breast or udder tissue, particularly in a mammary gland of a human female. The inflammation and/or infection is preferably mastitis.

10 Claims, 4 Drawing Sheets

LACTOBACILLUS SALIVARIUS FOR THE TREATMENT OF MASTITIS

CROSS-REFERENCE TO RELATED APPLICATIONS

This application is the National Phase of International Patent Application No. PCT/NL2014/050890, filed Dec. 19, 2014, published on Jun. 25, 2015 as WO 2015/093963 A1, which claims priority to International Patent Application No. PCT/NL2013/050924, filed Dec. 19, 2013. The contents of these applications are herein incorporated by reference in their entirety.

FIELD OF THE INVENTION

The present invention is in the field of therapy for mastitis in particular based on probiotics.

BACKGROUND OF THE INVENTION

Mastitis is inflammation or infection of breast or udder tissue, and can be classified as puerperal and nonpuerpural mastitis. Puerperal mastitis is associated with pregnancy, breastfeeding or weaning and occurs frequently in lactating mammals, both in animals and humans. Nonpuerpural mastitis has no relation to lactation, but has very similar symptoms, and may occur for example after nipple piercing. It is estimated that up to 33% of lactating women suffer from mastitis. Although mastitis may occur at any time during lactation, occurrences peak during the second and third week postpartum. The majority of mastitis is caused by *Staphylococcus* infection, mainly *S. aureus* and *S. epidermidis*. Treatment often involves administration of antibiotics. Mastitis is highly undesired, as the composition of the breast milk alters during mastitis, e.g. an increased content of sodium and inflammatory mediators, which may interfere with the optimal nutrition breast milk provides for the infant. Furthermore, during mastitis, continuing breastfeeding may not be possible or may not be desired by the mother.

SUMMARY OF THE INVENTION

It has now surprisingly been found that a strain of *Lactobacillus salivarius* designated as PS2 or a composition comprising the *Lactobacillus salivarius* PS2 effectively reduces mastitis and/or symptoms associated with mastitis. The *Lactobacillus salivarius* strain PS2 has been deposited and has been given accession number LMG P-27027.

DETAILED DESCRIPTION OF THE INVENTION

The invention relates to a new strain of *Lactobacillus salivarius*, compositions comprising this new strain and to a method for treatment and/or prevention of inflammation and/or infection in breast or udder tissue, in particular mastitis.

In a first aspect, the invention relates to a strain of *Lactobacillus salivarius*, having at least 80% sequence identity with the strain having accession number LMG P-27027.

In a second aspect, the invention relates to a composition comprising the strain of *Lactobacillus salivarius* according to the invention and a physiologically acceptable carrier or excipient. Preferably, the composition comprises $10^8$ to $10^{10}$ cfu *Lactobacillus salivarius* per gram dry weight. Preferably, the composition further comprises at least one selected from the group of non-digestible oligosaccharides, LC-PUFAs, further probiotics and micronutrients. Preferably, the composition is a powder.

In a third aspect, the present invention relates to the use of a strain of *Lactobacillus salivarius* according to the invention for the manufacture of a medicament. In other words, the invention relates to a strain of *Lactobacillus salivarius* according to the invention for use as a medicament. In other words, the invention relates to a method of preventing and/or treating a disease, comprising administering to a subject in need thereof a strain of *Lactobacillus salivarius* according to the invention.

In a fourth aspect, the present invention relates to the use of a composition according to the invention for the manufacture of a medicament. In other words, the invention relates to the composition according to the invention for use as a medicament. In other words, the invention relates to a method of preventing and/or treating a disease, comprising administering to a subject in need thereof the composition according to the invention.

In a fifth aspect, the present invention relates to the use of a strain of *Lactobacillus salivarius* according to the invention for the manufacture of a composition for the treatment and/or prevention of inflammation and/or infection of breast or udder tissue in a mammal. In other words, the invention relates to a strain of *Lactobacillus salivarius* according to the invention for use in the treatment and/or prevention of inflammation and/or infection of breast or udder tissue in a mammal. In other words, the invention relates to a method of treating and/or preventing inflammation and/or infection of breast or udder tissue in a mammal, comprising administering to a subject in need thereof a strain of *Lactobacillus salivarius* according to the invention. Preferably, the inflammation and/or infection of breast or udder tissue is mastitis. Preferably, the mammal is a human female. Preferably, the strain of *Lactobacillus salivarius* according to the invention is administered more than once per day, more preferably two or three times per day, most preferably three times per day, in a dose of $10^8$ to $10^{10}$ colony forming units (cfu) per dose.

In a sixth aspect, the present invention relates to the use of a composition according to the invention for the manufacture of a composition for the treatment and/or prevention of inflammation and/or infection of breast or udder tissue in a mammal. In other words, the invention relates to a composition according to the invention for use in the treatment and/or prevention of inflammation and/or infection of breast or udder tissue in a mammal. In other words, the invention relates to a method of treating and/or preventing inflammation and/or infection of breast or udder tissue in a mammal, comprising administering to a subject in need thereof a composition according to the invention. Preferably, the inflammation and/or infection of breast or udder tissue is mastitis. Preferably, the mammal is a human female. In one embodiment, the human female is at risk, in particular at high risk of developing mastitis, and the composition according to the invention is for prevention of mastitis in a human female at risk, in particular at high risk, of developing mastitis. Suitably, the human female has previously suffered from inflammation and/or infection in breast or udder tissue, in particular mastitis. Preferably, the composition according to the invention is administered more than once per day, more preferably two or three times per day, most preferably three times per day, in a dose of $10^8$ to $10^{10}$ colony forming units (cfu) per dose. Preferably, the composition further comprises at least one selected from the group of non-digestible oligosaccharides, LC-PUFAs, further probiotics and micronutrients.

Lactobacillus salivarius

The strain of *Lactobacillus salivarius* according to the invention is referred to as *Lactobacillus salivarius* PS2 or *L. salivarius* PS2. *L. salivarius* PS2 has been deposited by Danone Research BV, Bosrandweg 20, 6704 PH Wageningen, the Netherlands in accordance with the Budapest Treaty on the International Recognition of the Deposit of Microorganisms for the Purpose of Patent Procedure at the BCCM/LMG (Belgian Coordinated Collections of Microorganisms, Laboratorium voor Microbiologie—Bacteriënverzameling (LMG), University of Gent, K. L. Ledeganckstraat 35, B-9000 Gent, Belgium) on 23 May 2012. *L. salivarius* PS2 has been given BCCM/LMG accession number LMG P-27027. The depositor, Danone Research By, has authorised the applicant to refer to the deposited biological material in this patent application. Hereafter *L. salivarius* PS2 is also referred to as *Lactobacillus salivarius* LMG P-27027, or *L. salivarius* LMG P-27027.

The present invention also relates to strains of *L. salivarius* having at least 80% identity with the 16S rRNA sequence of the *L. salivarius* LMG P-27027 strain, preferably at least 85% identity, more preferably at least 90% identity, most preferably at least 95% identity (see: Stackebrandt & Goebel, 1994, *Int. J. Syst. Bacteriol.* 44:846-849). In a preferred embodiment, the strain according to the present invention has at least 97% identity with the 16S rRNA sequence of the *L. salivarius* LMG P-27027 strain, more preferably at least 98% identity, more preferably at least 99% identity. In another preferred embodiment, the strain according to the present invention has 100% identity with the 16S rRNA sequence of the *L. salivarius* LMG P-27027. In other words, in a preferred embodiment, the strain according to the present invention is the *Lactobacillus salivarius* strain LMG P-27027.

Composition

Preferably, the present strain of *L. salivarius* is comprised in a composition, such as a nutritional composition, a nutritional supplement, a pharmaceutical composition or a nutraceutical composition, preferably a nutritional composition or a nutritional supplement. Preferably, the present composition comprises the strain of *L. salivarius* and a physiologically acceptable carrier or excipient and/or further ingredients as described further below. Preferably, the strain of *L. salivarius* according to the invention is present in freeze-dried form.

The composition according to the invention preferably comprises $10^2$ to $10^{13}$ colony forming units (cfu) of the present strain of *L. salivarius* per gram dry weight of the composition, preferably $10^4$ to $10^{12}$, more preferably $10^5$ to $10^{11}$, most preferably from $10^5$ to $10^{10}$ cfu *L. salivarius* per gram dry weight of the composition. The *L. salivarius* strain according to the invention is preferably administered in a daily dose of $10^2$ to $10^{13}$, more preferably from $10^5$ to $10^{12}$, more preferably from $10^8$ to $5 \times 10^{10}$, most preferably from $10^8$ to $10^{10}$ colony forming units (cfu). The composition according to the invention may comprise viable and/or non-viable *L. salivarius* according to the invention, preferably viable *L. salivarius* according to the invention.

The present composition comprising the strain of *L. salivarius* may be in any form known in the art, such as in solid form, in semi-solid form or in liquid form. Preferably, the composition is a nutritional composition or a nutritional supplement, preferably in the form of a powder, capsule or tablet, most preferably a nutritional supplement. Suitable nutritional compositions include any beverage or food product, such as a drink, a milk-based beverage, a yogurt, a dairy product, a cereal product, a soy product, a fruit product, a vegetable product, a meat product or combinations thereof, e.g. a complete meal. In a preferred embodiment, the composition is a nutritional supplement in powder, capsule or tablet form, most preferably in powder form. Preferably, the composition comprises the strain of *L. salivarius* in freeze-dried form, which is especially suitable when the composition is in powder, capsule or tablet form. The present strain or the present composition may be contained within a container, preferably a stick or stickpack or a sachet. Preferably, the present composition, when in powder, capsule or tablet form, especially when in powder form, is intended to be added to a beverage or food product before ingestion. Preferably, the present composition, when in powder, capsule or tablet form, especially when in powder form, is accompanied with instructions to add the composition to a beverage or food product before ingestion. The beverage or food product to which the present composition is to be added may be any beverage or food product, such as a drink, a milk-based beverage, a yogurt, a dairy product, a cereal product, a soy product, a fruit product, a vegetable product, a meat product or combinations thereof, e.g. a complete meal.

Further Components

The strain of *L. salivarius* according to the invention is preferably present in a composition, which may comprise a physiologically acceptable carrier or excipient and/or further ingredients. Any physiologically acceptable excipient or carrier as known in the art may be used. Suitable excipients or carriers include, but are not limited to, water, glucose, lactose, sucrose, mannitol, maltodextrin, (resistant) starch, cellulose or cellulose derivatives, e.g. methylcellulose, magnesium stearate, stearic acid, sodium saccharin, talcum, magnesium carbonate and the like.

Preferably, further ingredients are included which are beneficial for lactating women, more preferably ingredients which are beneficial for the immune system and/or support the immune system. Those ingredients are generally known in the art and include, but are not limited to, dietary fibre and non-digestible oligosaccharides, LC-PUFAs and micronutrients (e.g. vitamins and minerals). Also macronutrients (e.g. lipids, protein, digestible carbohydrates) may be included in the composition according to the invention.

Non-Digestible Oligosaccharide

The present strain is preferably present in a composition, which further comprises non-digestible oligosaccharides. The term "non-digestible" as used in the present invention refers to saccharides which are not digested in the intestine by the action of acids or digestive enzymes present in the human upper digestive tract (small intestine and stomach), but which are fermented by the human intestinal flora. Mono- and disaccharides such as glucose, galactose, fructose, sucrose and lactose are digestible.

Preferably the present composition comprises non-digestible oligosaccharides with a degree of polymerization (DP) of 2 to 250, more preferably 3 to 60. Preferably the non-digestible oligosaccharides comprises at least one oligosaccharide selected from the group of fructo-oligosaccharides (such as inulin), galacto-oligosaccharides (such as transgalacto-oligosaccharides or beta-galacto-oligisaccharides), gluco-oligosaccharides (such as gentio-, nigero- and cyclodextrin-oligosaccharides), arabino-oligosaccharides, mannan-oligosaccharides, xylo-oligosaccharides, fuco-oligosaccharides, arabinogalacto-oligosaccharides, glucomanno-oligosaccharides, galactomanno-oligosaccharides, sialic acid oligosaccharides and uronic acid oligosaccharides, more preferably selected from the group of fructo-oligosaccharides, galacto-oligosaccharides and uronic acid oligosaccharides, most preferably selected from the group of fructo-oligosaccharides and galacto-oligosaccharides. Preferably, the composition comprises galacto-oligosaccharides, more preferably transgalacto-oligosaccharides. In a preferred embodiment the composition comprises a mixture of galacto-oligosaccharides and fructo-oligosaccharides.

The galacto-oligosaccharides preferably have a DP of 2 to 10. Preferably the galacto-oligosaccharides have an average DP of below 6. The galacto-oligosaccharide is preferably selected from the group consisting of transgalacto-oligosaccharides, lacto-N-tetraose (LNT), lacto-N-neotetraose (neo-LNT), fucosyl-lactose, fucosylated LNT and fucosylated neo-LNT. Transgalacto-oligosaccharides (TOS) are for example sold under the trademark Vivinal™ (Borculo Domo Ingredients, Netherlands). Preferably the saccharides of the transgalacto-oligosaccharides are β-linked. The fructo-oligosaccharide preferably have a DP of 2 to 250, more preferably 2 to 100, most preferably 5 to 60. Preferably the fructo-oligosaccharides have an average DP of above 10. Fructo-oligosaccharides include inulin, levan and/or a mixed type of polyfructan. An especially preferred fructo-oligosaccharide is inulin. Fructo-oligosaccharide suitable for use in the compositions is commercially available, e.g. as Raftiline®HP (Orafti). Preferably, the present composition comprises galacto-oligosaccharides and fructo-oligosaccharides in a weight ratio galacto-oligosaccharides:fructo-oligosaccharides of 99:1 to 1:99, more preferably 20:1 to 1:1, most preferably 12:1 to 7:1.

In another preferred embodiment, the composition comprises a mixture of short chain and long chain fructo-oligosaccharides. Preferably a mixture of fructo-oligosaccharides with an average DP below 10 and fructo-oligosaccharides with an average DP above 10. Fructo-oligosaccharide with an average DP below 10 suitable for use in the compositions is commercially available, e.g. as Raftilose®. Fructo-oligosaccharide with an average DP above 10 suitable for use in the compositions is commercially available, e.g. as Raftiline®HP. Preferably, the present composition comprises fructo-oligosaccharides with an average DP below 10 and fructo-oligosaccharides with an average DP above 10 in a weight ratio of 20:1 to 1:20, more preferably 10:1 to 1:10, most preferably 5:1 to 1:5 or in a ratio of about 1:1.

Preferably, the composition comprises 0.25 wt. % to 50 wt. % non-digestible oligosaccharides, more preferably 0.5 wt. % to 30 wt. %, even more preferably 1.0 wt. % to 20 wt. % non-digestible oligosaccharides based on dry weight. When in liquid form, the composition preferably comprises 50 mg to 5 g non-digestible oligosaccharides per 100 ml, more preferably 250 mg to 2 g, even more preferably 500 mg to 1 g per 100 ml. Expressed in dosage terms, the non-digestible oligosaccharide content is preferably 0.1 to 50 g per day, more preferably 1 to 35 g per day, even more preferably 5 to 25 g per day, most preferably 10 to 20 g per day.

Long Chain Polyunsaturated Fatty Acids (LC-PUFA)

Preferably, the present composition additionally comprises long chain polyunsaturated fatty acids and/or long chain polyunsaturated fatty acyl chains (LC-PUFAs). The term LC-PUFA in the present invention relates to a fatty acid or fatty acyl chain with a length of 20 carbon atoms or more and at least two unsaturated bonds. Preferably, the composition comprises an LC-PUFA selected from the group consisting of eicosapentaenoic acids and/or acyl chain (EPA), docosahexaenoic acid and/or acyl chain (DHA) and arachidonic acid and/or acyl chain (AA). In one embodiment the composition comprises DHA. In another embodiment the composition comprises EPA. More preferably the composition comprises DHA and EPA. LC-PUFA advantageously strengthen the immune system. Hence, administration of a composition comprising both dietary fibre and LC-PUFA to a lactating women will have an improved effect on the immune system.

Preferably the composition comprises 50 to 3000 mg LC-PUFA per daily dose, more preferably 100 to 1500 mg, most preferably 200 to 700 mg.

Micronutrients

Preferably the present strain is present in a composition that further comprises micronutrients, more preferably vitamins and minerals. Preferred micronutrients are those that are beneficial for lactating women, in particular those that are beneficial of the immune system and/or support the immune system. Those ingredients are generally known in the art and usually comprised in supplements intended for lactating women or young mothers. Inclusion of vitamins and minerals in the present composition conveniently reduces the amount of compositions or supplements to be taken by lactating women.

Preferred vitamins are the water-soluble vitamins; vitamin B1 (thiamine), vitamin B2 (riboflavin), vitamin B3 (niacin), vitamin B5 (pantothenic acid), vitamin B6 (pyridoxine), folic acid, vitamin B12 (cyanocobalamine), biotin, choline, and vitamin C, and the fat-soluble vitamins; vitamin D3, vitamin E and vitamin K. Most preferred vitamins are folic acid, vitamin B1, vitamin B2, vitamin B6, vitamin B12, choline and vitamin C.

Preferred minerals are calcium, phosphorus, zinc, iodine, iron, manganese, selenium, copper, and magnesium. Most preferred minerals are calcium, iodine, zinc and iron.

Further Probiotics

The composition according to the invention may comprise further probiotics, apart from the present strain of *L. salivarius* as described above.

Probiotics in the present invention refer to micro-organisms, which upon administration exert a beneficial effect on the host. Probiotics have beneficial effects on the immune system of lactating women, hence the combination with probiotics will have a superior effect on immune system. Preferably, the probiotics are selected from the group consisting of *Lactobacillus* and *Bifidobacterium*. More preferably, the probiotic is selected from the group consisting of the *Lactobacillus accidophilus* group, *L. rhamnosus, L. casei, L. paracasei, L. plantarum, L. reuteri, L. fermentum, Bifidobacterium infantis, B. animalis* subsp. *lactis, B. breve, B. longum* and *B. bifidum. Preferably, probiotics are present in a daily dose of* $1\times10^6$ colony forming units (cfu) to $1\times10^{13}$ cfu, more preferably $1\times10^7$ to $1\times10^{11}$, most preferably $1\times10^8$ to $1\times10^{10}$ of each individual probiotic.

In a preferred embodiment, the composition only comprises a single strain active in the treatment and/or prevention of mastitis, i.e. the strain of *L. salivarius* according to the invention. In one embodiment, the composition does not comprise a strain of *Lactobacillus gasseri*.

Macronutrients

The present composition may also comprise at least one, preferably at least two, more preferably at least three macronutrients selected from protein, fat and digestible carbohydrate. This is especially preferred in case the strain according to the invention is comprised in a nutritional composition. In an advantageous embodiment the present nutritional compositions comprise at least one selected from the group of non-digestible oligosaccharides, LC-PUFAs, further probiotics and micronutrients, as described above.

Application

The present strain and/or composition is suitable as medicament, in particular for the treatment and/or prevention of inflammation and/or infection of breast or udder tissue in a mammal, more in particular for the treatment and/or prevention of mastitis and/or symptoms associated with mastitis. Preferably, the present strain and/or composition is particularly suitable for the treatment of inflammation and/or infection of breast or udder tissue in a mammal, especially for the treatment of mastitis and/or symptoms associated with mastitis. In one embodiment, preferably the present strain and/or composition is particularly suitable for the prevention of inflammation and/or infection of breast or udder tissue in a mammal, especially for the prevention of mastitis and/or symptoms associated with mastitis. In the context of the present invention, "prevention" may also be worded as "reducing the risk of occurrence". As used herein, the phrase "treatment and/or prevention of mastitis and/or breast pain and other symptoms associated with mastitis" (and similar) include reducing the length of time a person suffers from mastitis, reducing the pain level experienced by the person suffering from mastitis, reducing the recovery time of the person suffering from mastitis, reducing the length of time (if any) that the person stops breast-feeding their infant due to mastitis, reducing the risk that the person chooses to stop breast-feeding due to mastitis, prolonging the length of time the person breast-feeds their infant and/or reducing the risk that the person stops breast-feeding their infant due to mastitis.

The mastitis to be treated and/or prevented may be puerperal or non-puerperal, preferably the mastitis is puerperal. Symptoms associated with mastitis include (local) breast pain, redness, swelling, breast engorgement and warmth of the breast(s), milk stasis, fever, flu-like symptoms and the development of breast abscesses. The present strain and/or composition may be administered to a woman who is suffering from mastitis or to a woman who is at risk, preferably at high risk, of developing mastitis. Women at high risk of developing mastitis include, but are not limited to, women who are lactating or are planning to start lactating and who have sore or cracked nipples, who have suffered from mastitis before (e.g. while breastfeeding another baby), who are breastfeeding at irregular intervals, who are taking or who have recently taken antibiotics (for another infection), who are suffering from diabetes, chronic illness, HIV infection, AIDS or an impaired immune system. In one embodiment, the present strain and/or composition is to be administered to women who have suffered from mastitis before. In the context of the present invention, "women" and "human females" is used interchangeably.

The present strain and/or composition may be administered to a woman who is planning to start lactating within a few weeks (e.g. four weeks prior to planned start of lactation), are lactating, or have recently stopped lactating. It is particularly preferred to administer the present strain and/or composition as long as the symptoms of mastitis prolong or, more preferably, as long as lactation continues In some embodiments, the present strain and/or composition may be administered to a woman in the last trimester of pregnancy (i.e. before they start breast-feeding their infant), in the first weeks post-partum, or for as long as lactation continues. Suitably, the present strain and/or composition may be administered to a woman from week 29 of her pregnancy onwards, from week 30, from week 31, from week 32, from week 32, from week 33, from week 34, from week 35, from week 36, from week 37, from week 38, from week 39, from week 40, from week 41, from week 42, from birth, or from any time post-partum while lactation continues either before or after any symptoms of mastitis are evident, onwards.

Mode of Administration

The composition used in the present method is preferably administered enterally, more preferably orally. The composition according to the invention may be administered in a single daily dose or multiple doses per day, such as at least 2 doses per day, at least 3 doses per day, at least 4 doses per day. Preferably, the composition according to the invention is administered more than once per day. In an especially preferred embodiment, the composition according to the invention is administered in 2 or 3 doses per day, most preferably in 3 doses per day. In a preferred embodiment, the composition according to the invention is a nutritional composition or a nutritional supplement. The supplement according to the invention may be in the form of a powder, a tablet (including chewable table) or a capsule. The nutritional composition according to the invention may be any food product or beverage. Preferably, the composition, especially the nutritional supplement, according to the invention further comprises a physiologically acceptable excipient or carrier. In a preferred embodiment, the composition or the supplement is a powder, packed in container (preferably a sachet) comprising 1 to 10 g, more preferably 1.5 to 7 g, most preferably 2 to 5 g. Preferably, each container contains a single dose.

Preferably, the nutritional composition is a milk-based liquid, comprising fats, proteins and digestible carbohydrates. Preferably this milk-based liquid is packed into a bottle or tetrapack with a volume of 50 to 1000 ml, more preferably 60 to 500, most preferably 75 to 125 ml.

Preferably, the composition is a powder, packed in a container, preferably a sachet, comprising 1 to 10 g, more preferably 1.5 to 7 g, most preferably 2 to 5 g.

In this document and in its claims, the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one".

BRIEF DESCRIPTION OF THE FIGURES

FIGS. 2a, 2b, 2c, and 2d show box plots of total bacterial counts of breast milk samples, obtained in the clinical trial of example 2, at day 0, day 7 and day 14; FIG. 2a=treatment group 1, FIG. 2b=treatment group 2, FIG. 2c=treatment group 3, FIG. 2d=reference group.

EXAMPLES

Example 1: Randomly Amplified Polymorphic DNA (RAPD) Analysis

A total of 28 *Lactobacillus salivarius* strains were submitted to Randomly Amplified Polymorphic DNA (RAPD) analysis. RAPD profiles were obtained using primer OPL5 (5'-ACGCAGGCAC-3') (Veyrat, A., Miralles, M. C. and Perez-Martinez, G. A. in *J. Appl. Microbiol.* 1999, 87:49-61). Computer assisted analysis was performed with Info-Quest FP software (Bio-Rad Laboratories, Inc., Hercules, Calif.).

The 28 analyzed strains included eleven strains isolated from human milk (PS2; HN6; FN 74 M1; LA 105 Te-1; WN 70 M1; AP 141 Me-2; AP 141 Me-11; TM 142 M1; TA 143 Ma-1; TA 143 Te-1; MV 144 M1), one strain isolated from infant feces (ZH17-05), one strain isolated from porcine milk (CELA-2), one strain isolated from poultry (CTC 2197), ten strains obtained from human vaginal exudates (V3-III-1; V4-II-90; V7-II-1; V7-II-62; V7-IV-1; V7-IV-60; V8-III-62; V11-I-60; V11-III-60; V11-IV-60), five strains from known collections (FI 9810; FI 9789; CECT 4062; CECT 4063; CECT 5713).

Figure 1:
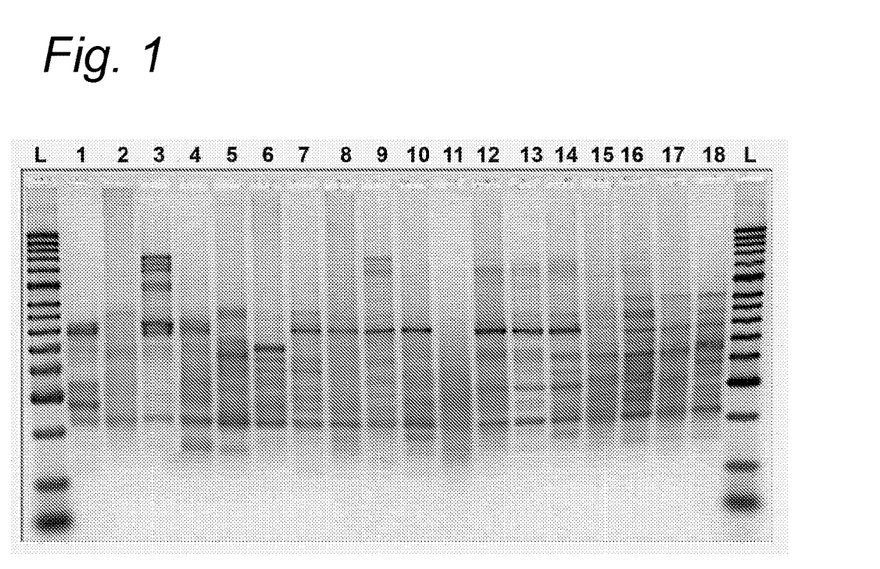
FIG. 1 shows RAPD analyses of 18 different strains of *Lactobacillus salivarius*. The lanes correspond to: (1) ZH17-05; (2) CELA-2; (3) PS2; (4) CECT 5713; (5) CTC 2197; (6) FI 9810; (7) FI 9789; (8) CECT 4062; (9) CECT 4063; (10) V3-III-1; (11) V4-II-90; (12) V7-II-1; (13) V7-II-62; (14) V7-IV-1; (15) V7-IV-60; (16) V8-III-62; (17) V11-I-60; (18) V11-III-60; (L) HyperLadder™ II (50 bp-2000 pb) (Bioline).
Figure 2A:
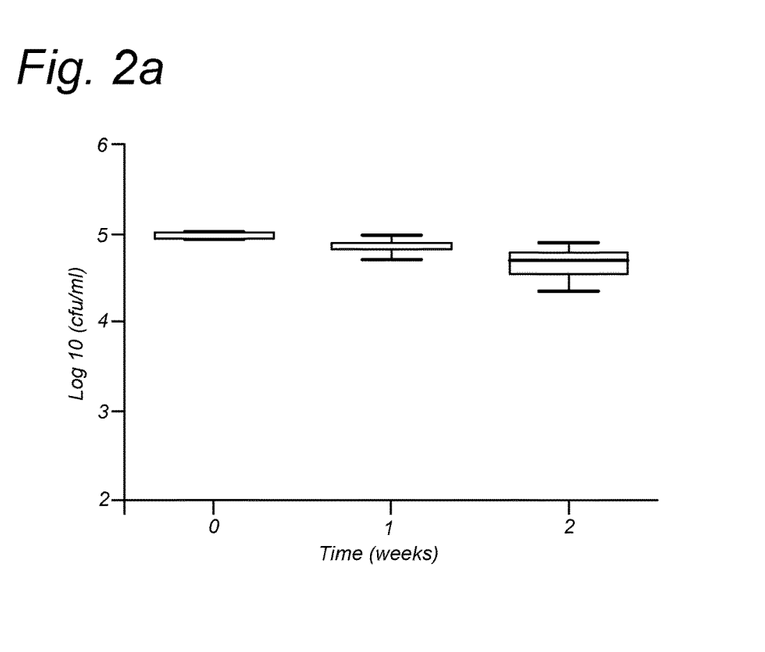
Figure 2B:
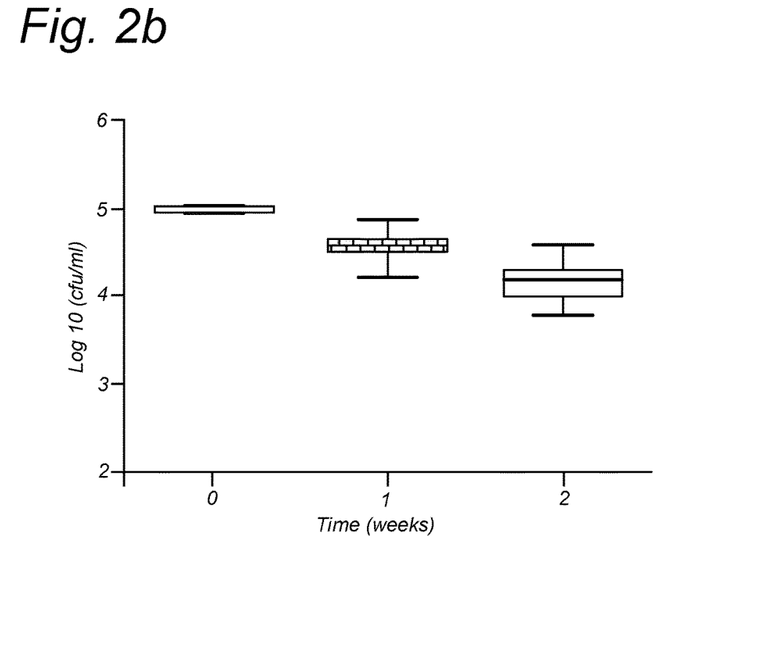
Figure 2C:
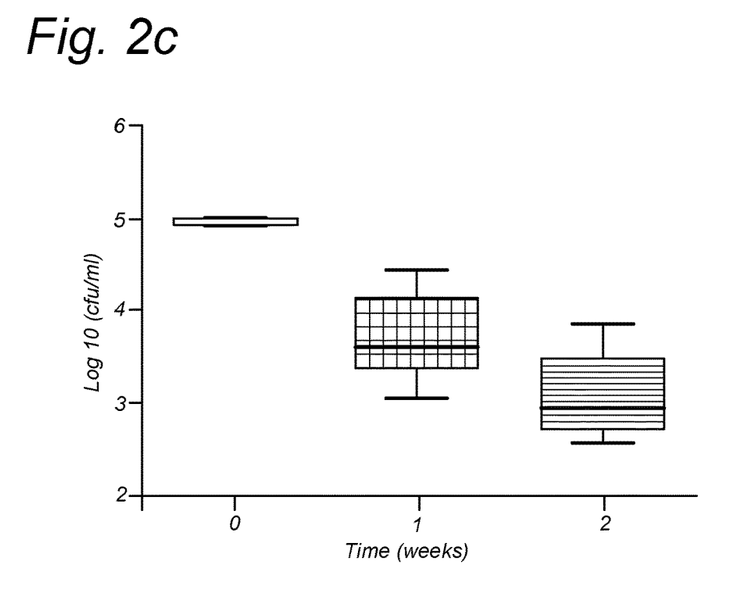
Figure 2D:
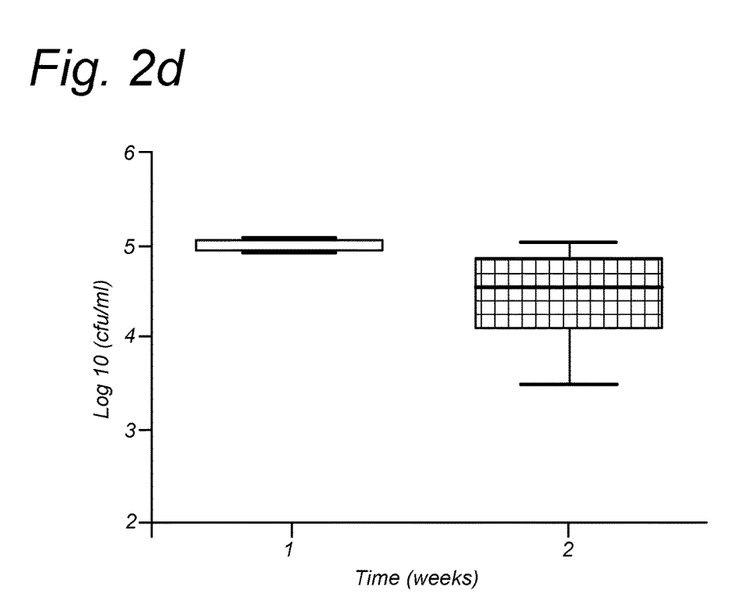

The analysis revealed that the RAPD profile of *Lactobacillus salivarius* PS2 (lane 3) was different to those of the other strains studied here, see FIG. 1 for a selected comparison (other RPAD profiles not shown).

Arroyo et al. in *Clin. Infect. Dis.* 2010, 50(12), 1551-1558, describe the use of a bacterial strain *Lactobacillus salivarius* CECT5713 in treating mastitis. The *Lactobacillus salivarius* PS2 strain that is the subject of the present invention was shown here to have a different RAPD profile to the CECT5713 strain, and also to have improved properties compared to the CECT5713 strain, such as increased stability and absence of prophages in its genome (Langa et al. in *Appl. Microbiol. Biotechnol.* 2012, 94, 1279-87).

Example 2: Clinical Trial I

Treatment of Mastitis

Methods:

An open-labeled study was performed with a total of 108 lactating women with symptoms of mastitis. All met the following criteria: breast inflammation, painful breastfeeding, milk bacterial count >1×10$^4$ cfu/mL. The lactating women received either 1 (treatment group 1, n=25), 2 (treatment group 2, n=25) or 3 (treatment group 3, n=25) capsules containing a freeze-dried probiotic supplement comprising 1×10$^9$ cfu *L. salivarius* PS2 per g per day during 14 days. The reference group (n=33) received antibiotic treatment for 14 days as prescribed in their primary care centers. None of subjects ingested commercial probiotic foods or supplements during the study. Women with mammary abscesses, Raynaud syndrome, or any other mammary pathology were excluded.

Breast milk samples were taken before the supplementation or treatment started (day 0) and every week until the end of the study (day 7 and day 14). The evolution of the symptoms was evaluated at the same time points by midwifes in their primary care centers; the volunteers were asked to score their breast pain from 0 (extremely painful) to 10 (no pain).

Bacterial count was measured in the milk samples as follows. Samples were spread onto Baird-Parker, Columbia, Mac-Conkey, and Sabouraud dextrose chloramphenicol agar plates for selective isolation and quantification of the main agents involved in infectious mastitis and, parallel onto agar plates of MRS (Oxoid) supplemented with L-cysteine (0.5 g/L) (MRS-Cys) for isolation of lactobacilli. The plates were incubated for 48 hours at 37° C. in aerobic conditions, except for the MRS-Cys plates, which were incubated anaerobically.

Bacteria isolated from milk were initially identified at the species level by classic morphological and biochemical tests. The identification of bacteria belonging to the *S. epidermidis* or *S. aureus* species was confirmed by a multiplex polymerase chain reaction (PCR) method based on dnaJ genes. Identification of streptococci was performed by partial amplification and sequencing of the gene tuf. The remaining isolates were identified by 16S rRNA sequencing. Their identity was determined on the basis of the highest scores (>99%) among the sequences deposited in the European Molecular Biology Laboratory database.

Identification of *L. salivarius* PS2 in the milk samples was done by a DNA-DNA colony hybridization assay. For this purpose, 2 species-specific probes were designed on the basis of unique 16S rRNA sequences. Colonies obtained on MRS-Cys plates from milk samples (day 14) were spotted in a regular array on 2 sets of MRS-Cys replica plates. Then, nylon Hybond-N+ discs (GE Healthcare) were laid directly on the culture surfaces and were kept there for 1 minute. Both hybridization and detection were performed as previously described (Jimenez et al. in *Appl. Environ. Microbiol.* 2008, 74: 4650-4655). The identity of the isolates that gave a positive signal after colony hybridization was confirmed by 16S rRNA sequencing as described above and were submitted to pulsed-field gel electrophoresis (PFGE) genotyping as previously described (Jimenez et al., 2008). Their profiles were compared with those of *L. salivarius* CECT4062, *L. salivarius* CECT4063, *L. salivarius* DSM 20492 and *L. salivarius* CECT5713.

Statistical Analysis:

Microbiological data, recorded as number of cfu per mL of milk, were transformed to logarithmic values before statistical analysis. The reported values of bacterial counts are the mean values of duplicate or triplicate determinations. The continuous variables "bacterial counts" and "breast pain score" were not normally distributed. Mann Whitney tests were performed to determine statistically significant differences between the bacterial counts (total and main bacterial species) and between the breast pain scores at different time points of the trial.

Bacterial Counts in the Milk Samples:

At day 0, the mean values of total bacterial count in milk were very similar in the 4 groups and ranged from 8.5 to 1.2×10$^4$ cfu/mL (Table 1). On day 7, the mean values of the total bacterial counts in treatment groups 2 and 3, receiving 2 or 3 doses per day, were significantly lower (p<0.001) than the corresponding value in treatment group 1, receiving one dose per day. This parameter was not analyzed in the reference group at 7 days. On day 14, the mean values of the total bacterial counts in the reference group tended to be significantly lower than in treatment group 1. However, treatment groups 2 and 3 had significantly lower mean values of the total bacterial count than the reference group, see Table 1 and FIG. 2.

TABLE 1

Mean total bacterial counts (TBC) in the treatment and reference groups.

| | TBC in $10^3$ cfu/mL (standard deviation) | | |
|---|---|---|---|
| | day 0 | day 7 | day 14 |
| treatment group 1 | 97.5 (8.0) | 74.3 (11.5) | 49.8 (16.1) |
| treatment group 2 | 99.0 (4.1) | 38.4 (12.8) | 15.9 (7.7) |
| treatment group 3 | 97.7 (4.8) | 8.2 (7.5) | 2.1 (2.3) |
| reference group | 98.6 (8.0) | n.d. | 40.1 (34.0) | n.d. = not determined

Figure 3A:
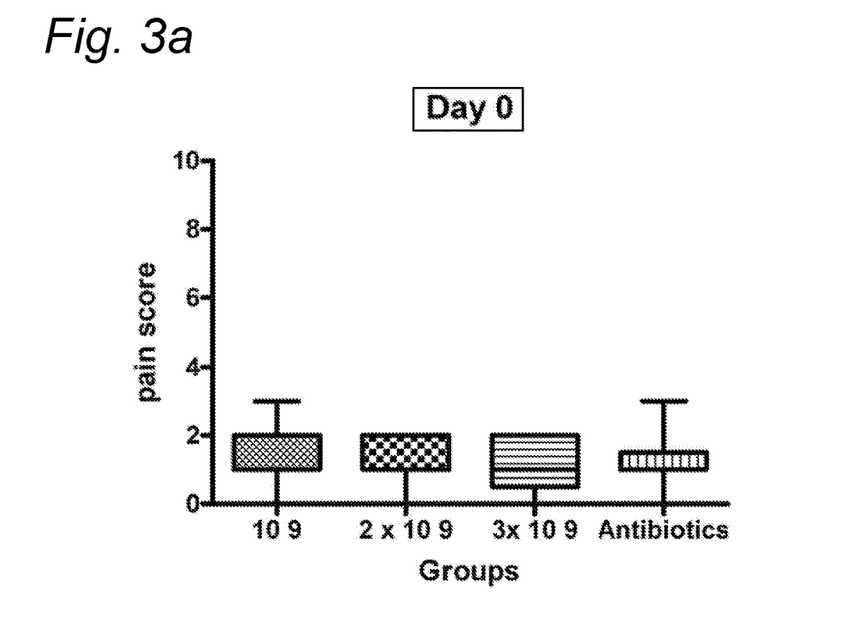
FIGS. 3a and 3b show box plots of the pain scores, obtained in the clinical trial of example 2, at day 0 (FIG. 3a) and at day 14 (FIG. 3b).
Figure 3B:
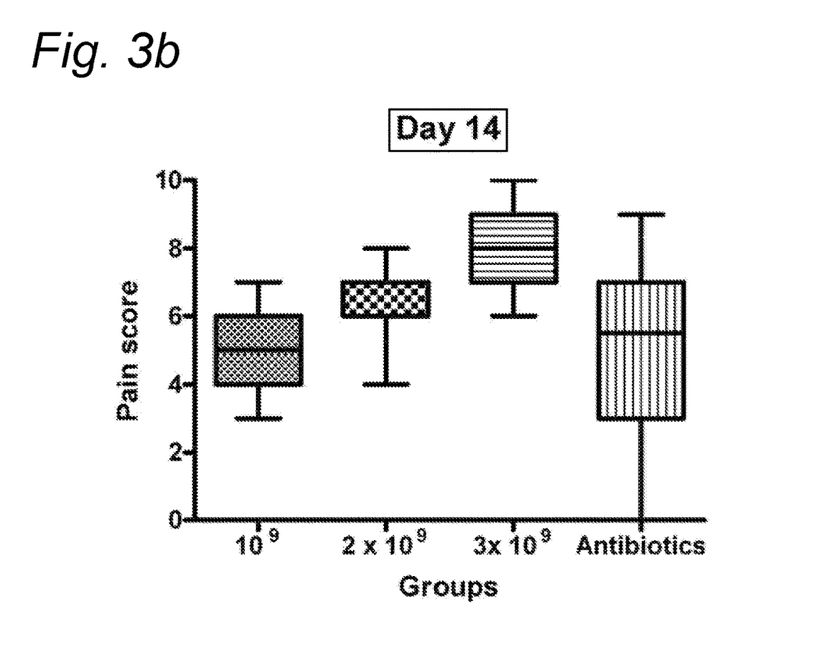

Evolution of the Clinical Symptoms:

The mean score of breast pain reported by the women was similar at day 0 in the 4 groups, ranging from 0 to 3, see Table 2 and FIG. 3a. At day 14, the breast pain score had improved in most of the participants. There were statistically significant differences (p<0.001) between the breast pain scores in treatment group 2 and 3, receiving 2 and 3 doses per day (mean score of 6.5 and 8.2 respectively) and the breast pain score in treatment group 1 (mean score of 4.08 and 5.03, respectively) at day 14, see Table 2 and FIG. 3b.

TABLE 2

Mean breast pain scores (BPS) in the treatment and reference groups.

| | BPS (standard deviation) | | |
|---|---|---|---|
| | day 0 | day 7 | day 14 |
| treatment group 1 | 1.2 (0.8) | 2.9 (0.9) | 4.8 (1.1) |
| treatment group 2 | 1.1 (0.7) | 4.8 (1.1) | 6.5 (0.9) |
| treatment group 3 | 1.0 (0.8) | 6.8 (1.4) | 8.2 (1.2) |
| reference group | 1.1 (0.8) | n.d. | 5.0 (2.5) | n.d. = not determined

Conclusion:

These results indicate that supplementation with *L. salivarius* PS2 resulted in a reduced bacterial count in breast milk and an improvement of clinical symptoms (pain score) of women suffering from mastitis. Results obtained with one daily dose of $10^9$ cfu/mL *L. salivarius* PS2 are comparable with those obtained with antibiotics, while two or three daily doses of $10^9$ cfu/mL *L. salivarius* PS2 clearly performs better than regular treatment with antibiotics. Supplementation with two or three doses, in particular with three doses, of this strain per day resulted in significantly larger reduction of the bacterial count when compared to standard antibiotic treatment.

Example 3: Clinical Trial II

Prevention of Mastitis in High-Risk Subjects

Methods:

A randomized, double blind, placebo-controlled intervention study was performed with a total of 108 healthy pregnant women, aged 25-35, intending to breastfeed their infants. All met the following criteria: normal pregnancy, healthy status and a history of lactational mastitis after, at least, a previous pregnancy. Subjects were randomized in a test group (n=55) and a placebo group (n=53). The test group ingested 1 sachet containing freeze-dried probiotic powderous supplement comprising $1 \times 10^9$ cfu *L. salivarius* PS2 per g per day, and the placebo group ingested 1 sachet containing a placebo supplement, from the 30$^{th}$ week of pregnancy until 12 weeks after delivery. None of subjects ingested commercial probiotic foods or supplements during the third trimester of the pregnancy and during the study. Women ingesting commercial probiotic foods or supplements or receiving an antibiotic treatment in the previous 30 days, and women with allergy to cow's milk protein or intolerance to lactose and women with mammary abscesses, Raynaud syndrome, or any other mammary pathology are excluded.

Mastitis symptoms were assessed by midwifes of Primary Health Centers during the first 3 months after birth. Following recent criteria for the classification of infectious mastitis [Fernández et al., *Benef. Microbes*. 2014, 5(2), 169-83], "acute mastitis" was defined as an acute inflammation of the breast with local (ingurgitation, pain, redness, reduced secretion) and systemic (flu-like) symptoms while "subacute mastitis" was defined as a breast inflammation characterized by the presence of local symptoms (ingurgitation, needle-like and/or burning pain, reduced secretion) and the absence of systemic symptoms. Both definitions only include those cases associated to a high milk bacterial count (>$10^3$ CFU/mL), determined as explained below, and a high milk leukocyte count (>$10^4$ cells/mL). Leukocyte quantification was performed by optical microscopy after May-Grünwald-Giemsa differential staining.

When mastitis occurred, the volunteers were asked to score their breast pain feeling from 0 (extremely painful) to 10 (no pain), following a standard pain scoring procedure [Jensen and Karoly, Handbook of Pain Assessment, 2nd edition, New York: Guilford Press, 2001, pp 15-34; Jensen, *Pain assessment in clinical trials*. In H. Wittink and D. Carr (eds.), Pain Management: Evidence, Outcomes, and Quality of life. Amsterdam: Elsevier, 2008].

Breast milk samples (10 mL) were collected between 91 and 100 days after birth in the case of the women that did not suffer mastitis during the 3-month follow up period. In the case of women that suffered such condition, a milk sample was collected immediately after diagnosis. Bacterial count is measured in the milk samples as follows. Samples are spread onto Baird-Parker, Columbia, Mac-Conkey, and Sabouraud dextrose chloramphenicol agar plates for selective isolation and quantification of the main agents involved in infectious mastitis and, parallel onto agar plates of MRS (Oxoid) supplemented with L-cysteine (0.5 g/L) (MRS-Cys) for isolation of lactobacilli. The plates are incubated for 48 hours at 37° C. in aerobic conditions, except for the MRS-Cys plates, which are incubated anaerobically. Bacteria isolated from milk are initially identified at the species level by classic morphological and biochemical tests. After bacterial counting, representatives of each colony morphology type were identified by MALDI-TOF by spotting a portion of a bacterial colony (~1 μL) onto a MALDI sample plate. Then, it was overlaid with 1 μL of a saturated solution of α-cyano-4-hydroxycinnamic acid in acetonitrile (28%), and allowed to dry at room temperature. For each isolate, a mean spectrum was constructed with at least 50 m/z spectra profiles and used for the identification by comparison with the spectra contained in the Myla database (Biomerieux). Identification was defined as a 99-100% match to the species-specific m/z values in the database.

Statistical Analysis:

Microbiological data, recorded as number of cfu per mL of milk, were transformed to logarithmic values before statistical analysis. Continuous variables were expressed as means and 95% confidence interval (CI) of the means after checking for normality. A one-way ANOVA analysis followed by a Bonferroni post-test was used for comparison of age and starting time (week of pregnancy) of the study between probiotic and placebo groups, and to check the effect of the probiotic intervention and the type of mastitis (subacute and acute) in the breast pain scores. A two-way ANOVA analysis was used to investigate the effect of treatment and mammary gland health status on staphylococcal/streptococcal counts as well as the effect of treatment and mastitis type on breast pain score and to study the possible interaction of the two investigated variables. Proportions were compared using $\chi^2$ or Fisher exact probability tests when required. A correlation analysis was performed to test the relationship between staphylococcal/streptococcal counts in breast milk and the breast pain score. Statistical significance was set at P<0.05.

Results:

There were no significant differences between the probiotic and the placebo group regarding the age (mean: 31.18 years, 95% CI: 30.70-31.66 for the probiotic group and mean: 30.51 years, 95% CI: 30.02-31.00 for the placebo group; P=0.1699, one-way ANOVA) and the week of pregnancy (mean: 29.82 week, 95% CI: 29.49-30.15 for the probiotic group and mean: 30.06 week, 95% CI: 29.74-30.37 for the control group; P=0.2953, one-way ANOVA) at the start of the study. No adverse or side effects/events related to the ingestion of the probiotic were reported throughout the study.

The occurrence of mastitis was evaluated during the first 3 months after delivery. Globally, 44 women out of 108 (59.26%) suffered mastitis; 77.27% of the cases were classified as subacute, while acute cases accounted for the remaining 22.73%. The results of the incidence of (subacute or acute) mastitis within the first three months after delivery are presented in Table 3, as well as the mean total bacterial counts (TBC) in the breast milk and breast pain scores (BPS). Statistically significant differences were found between the probiotic and the control group in relation to the mastitis frequency. The percentage of women suffering mastitis in the probiotic group was significantly lower than in the control group (P=0.0010, $\chi^2$ test). No significant differences were found between the group of women that had been receiving L. salivarius PS2 during their pregnancy and the control group that received a placebo regarding the type of mastitis. In the probiotic group, the frequencies of subacute and acute mastitis were 79% and 21%, respectively, while in the control group these percentages were 77% and 23%, respectively (P=1.000, Fisher exact probability test).

The mean bacterial count in the milk samples provided by all the participants was 2.63×10³ CFU/mL (95% CI: 1.74× 10³ 3.98×10³). Both the consumption of probiotic or placebo and the healthy status of the mammary gland (healthy, subacute mastitis or acute mastitis) had a significant effect (P=0.000 for both main factors, two-way ANOVA) on the bacterial counts detected in breast milk. Furthermore, the interaction between this two factors was also highly significant (P=0.000, two-way ANOVA), indicating that the mean bacterial counts found in breast milk from healthy women and women with mastitis depended strongly on the probiotic treatment.

When the bacterial counts recorded in milk samples from healthy women that had received the probiotic (n=41) were compared with those of the healthy women included in the control group receiving the placebo (n=23), a small but significant difference was observed (P=0.0005, t-test). The differences observed between both groups in the bacterial counts of milk obtained from women with subacute and acute mastitis were higher: the mean bacterial counts in the probiotic subacute (n=11) and acute (n=3) groups were 6.76×10³ CFU/mL and 6.17×10³ CFU/mL respectively, while the mean bacterial counts in the placebo subacute (n=23) and acute (n=7) groups amounted to 4.07×10⁴ CFU/mL subacute (n=11) and 1.05×10⁵ CFU/mL respectively (P=0.0001 and 0.0064 respectively, t-test) (Table 3). No significant differences were found when the bacterial counts of breast milk samples obtained from subacute cases when compared with those from acute cases both in the probiotic (P=0.770, t-test) or the placebo (P=0.0939, t-test) groups.

TABLE 3

Results of clinical trial II

|  | test group (n = 55) | placebo group (n = 53) | P |
|---|---|---|---|
| incidence of no mastitis | n = 41 (75%) | n = 23 (43%) |  |
| incidence of mastitis (total) | n = 14 (25%) | n = 30 (57%) | .0010 [b] |
| incidence of subacute mastitis | n = 11 (79%) | n = 23 (77%) | 1.000 [c] |
| incidence of acute mastitis | n = 3 (21%) | n = 7 (23%) | 1.000 [c] |
| TBC [a] (no mastitis) | 0.50 | 0.69 | .0005 [d] |
| TBC [a] (subacute mastitis) | 6.76 (5.01-9.33) | 40.7 (24.0-70.8) | .0001 [d] |
| TBC [a] (acute mastitis) | 6.17 (1.95-19.5) | 105 (32.4-339) | .0064 [d] |
| BPS (subacute + acute mastitis) | 2.77 (2.16-3.38) | 1.40 (0.93-1.87) | .0012 [e] |

[a] mean and 95% confidence interval in 10³ cfu/mL;
[b] $\chi^2$ test;
[c] Fisher exact probability test;
[d] t-test;
[e] one-way ANOVA.

Most of the participants that suffered mastitis (43 out of 44) scored their breast pain between 0 and 4 in a scale ranging from 0 (extremely painful) to 10 (no pain). There was a strong correlation between the BPS reported and the bacterial counts found in milk (r=−0.814, P=0.000, Pearson product-moment correlation). A two-way ANOVA test contrasting all observations recorded for the breast pain reported by the participant women with mastitis showed that the consumption of L. salivarius PS2 had a significant effect on the intensity of the pain, in contrast with the mastitis type (Table 8). Higher BPS values, which indicates less intense pain, were reported by women in the probiotic group (n=13) than by those in the placebo group (n=30). Generally, the type of mastitis did not cause significant differences in the breast pain score (mean BPS=1.97; 95% CI: 1.50-2.44 in 33 women with subacute mastitis vs. mean BPS=1.30; 95% CI: 0.40-2.20 in 10 women with acute mastitis; P=0.1663, one-way ANOVA). Among all women with mastitis, those reporting to suffer more intense breast pain (lower BPS) were more frequently found in the placebo than in the probiotic group (P=0.0327, $\chi^2$ test). In fact, all women (n=9) that indicated to feel her breast extremely painful (BPS=0) did not take L. salivarius PS2 and were included in the placebo group.

Conclusion:

L. salivarius PS2 administration causes significant reduction in occurrence of mastitis, total bacterial counts of the maternal milk (for healthy women, women suffering from subacute and acute mastitis) and breast pain scores of women suffering from mastitis, even for the target group of women at high risk of developing mastitis. The strain according to the invention is thus capable of preventing mastitis.

Example 4: Clinical Trial III

Treatment of Mastitis

Methods:

A total of 23 women with symptoms of mastitis participated in the study. All met the following criteria: breast inflammation, painful breastfeeding, milk staphylococcal/streptococcal count >3 $\log_{10}$ colony forming units (CFU)/mL, and milk leukocyte count >4 $\log_{10}$ cells/mL. All subjects consumed daily, for 21 days, ~9.5 $\log_{10}$ CFU of *Lactobacillus salivarius* PS2. None of subjects ingested commercial probiotic foods or supplements during the study. Women with mammary abscesses, Raynaud syndrome, or any other mammary pathology were excluded.

Mastitis symptoms were assessed at days 0 and 21 by midwifes of Primary Health Centers. Breast milk, blood and urine samples were obtained at the beginning and at the end of the study. Milk samples (30 mL) were collected between 7-9 a.m. and at least 2 h after the last feeding. The first 2 mL was collected by manual expression for microbiological analysis and somatic cell count while the rest of the milk was obtained using a breast pump for biochemical and immunological analyses. The first 22 mL-fraction of the blood samples was collected into a Na-heparin tube to analyze the fatty acid (FA) composition of the cellular fraction and oxidative stress (0S)-related parameters in plasma. A second fraction of 8 mL was collected in EDTA tubes for standard hematology and immunological analysis The last 4 mL was used to obtain serum for standard biochemistry and quantification of the high sensitive C-reactive protein (hs-CRP). The first morning urine was collected for standard urinalysis (density, pH, proteins, glucose, ketone bodies, nitrites, urobilinogen, red blood cells and leukocytes).

Bacterial count was measured in the milk samples as follows. Samples were spread onto Baird-Parker, Columbia, Mac-Conkey, and Sabouraud dextrose chloramphenicol agar plates and incubated for 48 h at 37° C. in aerobic conditions for selective isolation and quantification of the main agents involved in infectious mastitis. After bacterial counting, representatives of each colony morphology type were identified by MALDI-TOF. Fresh milk samples were used for somatic cell count (SCC) using an automatic cell counter. The analysis of somatic cells subsets was performed by optical microscopy after May-Grünwald-Giemsa differential staining of fresh milk. The analysis was performed in duplicate by two different observers and a minimum of 100 cells were counted for each sample. Fat, protein, lactose, total solids and non-fat solids (NFS) concentrations of the milk samples were determined using a MilkoScan Minor instrument, previously calibrated and validated for human milk analysis. Sodium, potassium and chloride concentrations were determined in defatted milk samples using ion-selective electrodes on a Spotlyte analyzer. After thawing, 0.5 mL of each milk sample was spiked with 0.5 mL of 40 mM NaCl solution. Each measure was repeated three times.

Fatty acids (FA) present in milk samples and in the blood cell fraction were directly derivatized to FA methyl esters (FAME) and analyzed as described previously [Rodríguez-Alcalá et al., *Innov. Food Sci. Emerg. Technol.* 2009, 10, 32-36]. Analyses were carried out at least in duplicate. Concentrations of a wide spectrum of cytokines, chemokines, growth factors and immunoglobulins in milk and blood samples were determined in duplicate using a Bioplex 200 system instrument or by ELISA as described previously [Espinosa-Martos et al., *J. Pediatr. Gastroenterol. Nutr.* 2013, 56, 560-8]. Lewis blood antigens were also analyzed in plasma samples. Metabolites related to osmotic stress and nitric oxide metabolism end products (NOx) in blood were measured in duplicate as described previously [Codoñer-Franch et al., *Atherosclerosis* 2011, 215, 475-480 and *Nutr. Metab. Cardiovasc. Dis.* 2012, 22, 237-243].

Statistical Analysis:

Microbiological data, recorded as number of cfu per mL of milk, were transformed to logarithmic values before statistical analysis. Shapiro-Wilk tests were used for the normality check. Concentrations were expressed as means and 95% confidence interval (CI) in normally distributed data or as medians and interquartile range (IQR) when they were not. The effect of probiotic intervention was analyzed by paired Student t-tests or Wilcoxon signed-rank-tests. Differences in the detection frequencies of analytical parameters were analyzed using $\chi^2$ tests with Yates correction when required. Differences were considered significant at $P<0.05$.

Milk Analyses:

The analyses of the milk samples are summarized in Tables 4 and 5. At day 0, the mean total bacterial count in the milk samples was 4.08 $\log_{10}$ CFU/mL; this value significantly decreased at the end of the study (3.09 $\log_{10}$ CFU/mL; P<0.000) (Table 4). Importantly, the counts of all microorganisms involved in mastitis (*Staphylococcus epidermidis, Staphylococcus aureus, viridans* streptococci, and corynebacteria) decreased significantly on day 21 (Table 4), while Lactobacilli, which could not be detected on milk samples collected on day 0, were isolated in more than half of the women on day 21 (data not shown). Clinical symptoms disappeared or notably improved among all women at the end of the study (data not shown). Globally, the SCC values did not change, although a significant decrease in the percentage of polymorphonuclear (PMN) leukocytes (P=0.018) and a downward trend in the percentage of epithelial cells were observed after the probiotic treatment (Table 4). Breast milk concentrations of fat, lactose, total solids and non-fat solids did not change throughout the study period, and although the protein content was lowered on day 21, this was still within normal physiological values (data not shown). Milk potassium levels were reduced (P=0.000) and those of chloride increased (P=0.002) after the probiotic intervention, while milk sodium concentrations as well as the Na/K ratio were not modified (Table 4). The principal fatty acid found in breast milk samples was oleic acid (C18:1 c9, ~40%), followed by palmitic (C16, ~15-17%), linoleic (C18:2 c9, c12, ~13-14%), and lauric (C12, ~10%) acids (data not shown). No changes were found in FA composition of milk after the treatment, except for a small increase observed in palmitic acid (1.9%, P=0.018).

IgA, IgG1, IgG3, IgG4, and IgM were the immunoglobulines most frequently detected in the milk samples. IgA was detected in all the samples and at the highest concentrations (Table 5). After the probiotic treatment, levels of IgE and IgG3 increased significantly (P=0.041 and 0.020, respectively) (Table 5). Cytokines, chemokines and growth factors were found in breast milk samples at substantially different frequencies: IL-1$\beta$, TGF-$\beta_2$, GRO-$\alpha$, IL-8, MCP-1, MIP-1$\beta$, and EGF could be detected in more than 90% of the samples, IL-6, IL-7 and GM-CSF in 57-87%, and the rest of these compounds in less than 50% of them (Table 5). The probiotic intake did not modify neither their observed frequencies of detection nor their concentrations, except for IL-7 and EGF that increased significantly (P=0.070 and 0.061, respectively) (Table 5). Interestingly, the mean concentration of cytokines IFN-$\gamma$, IL-1$\beta$, IL-6, IL-10, IL-12 (p70), and TNF-$\alpha$, and chemokines IL-8, MCP-1 and MIP-1$\beta$ were lower and their confidence interval values narrower after the intervention, although these changes did not reach statistical significance (Table 5).

TABLE 4

Bacterial, somatic cell and electrolyte contents in milk

| | Initial (day 0) | | Final (day 21) | | |
|---|---|---|---|---|---|
| | n | mean (95% CI [b]) | n | mean (95% CI [b]) | P [a] |
| Bacterial count ($\log_{10}$ CFU/mL) | | | | | |
| *S. epidermidis* | 23 | 3.59 (3.33-3.85) | 23 | 2.83 (2.59-3.06) | .000 |
| *S. aureus* | 10 | 0.87 (0.33-1.41) | 6 | 0.22 (−0.13-0.56) | .002 |
| *Streptococcus* sp. | 21 | 2.99 (2.53-3.46) | 20 | 1.97 (1.61-2.33) | .000 |
| *Corynebacterium* sp. | 11 | 0.45 (0.08-0.82) | 5 | 0.03 (−0.23-0.28) | .001 |
| Total bacteria count | 23 | 4.08 (3.89-4.28) | 23 | 3.09 (2.90-3.28) | .000 |
| Somatic cell count ($\log_{10}$ cell/mL) | | | | | |
| Total cell count | | 7.94 (7.77-8.11) | | 8.04 (7.92-8.16) | .689 |
| Live cell count | | 7.30 (7.14-7.46) | | 7.30 (7.17-7.43) | .648 |
| Viability (%) | | 21.32 (18.74-23.91) | | 19.65 (17.17-22.12) | .600 |
| Somatic cell subtype (%) | | | | | |
| Monoc./Macroph. [c] | | 13.84 (9.90-17.77) | | 17.49 (11.98-23.00) | .163 |
| Lymphocytes | | 77.36 (72.11-82.61) | | 77.98 (72.77-83.20) | .346 |
| PMN leukocytes | | 6.11 (4.93-7.28) | | 2.62 (0.78-4.46) | .018 |
| Epithelial cells | | 2.63 (0.87-4.29) | | 1.83 (0.63-3.03) | .102 |
| Electrolyte concentration (mM) | | | | | |
| Sodium (Na) | | 14.54 (12.34-16.75) | | 14.16 (12.40-15.93) | .665 |
| Potassium (K) | | 13.77 (13.14-14.41) | | 12.70 (12.19-13.21) | .000 |
| Chloride | | 21.94 (18.14-25.73) | | 28.40 (23.44-33.36) | .002 |
| Na/K ratio | | 1.08 (0.90-1.25) | | 1.13 (0.98-1.28) | .447 |

[a] paired t-test;
[b] 95% confidence interval;
[c] Monocytes/Macrophages.

TABLE 5

Concentrations of immunoglobulins and cytokines in milk

| | Initial (day 0) | | Final (day 21) | | |
|---|---|---|---|---|---|
| | n | mean (95% CI [b]) | n | mean (95% CI [b]) | P [a] |
| Immunoglobulins (mg/L) [c] | | | | | |
| IgA ($\times 10^3$) | 23 | 3.90 (3.31-4.49) | 23 | 3.77 (3.32-4.20) | .543 |
| IgE | 11 | 0.29 (0.12-0.45) | 12 | 0.50 (0.27-0.73) | .041 |
| IgG1 | 21 | 52.24 (41.42-63.06) | 21 | 50.10 (36.66-63.54) | .788 |
| IgG2 | 9 | 282.85 (83.89-481.82) | 10 | 285.93 (109.87-461.98) | .441 |
| IgG3 | 17 | 17.54 (11.39-23.68) | 17 | 25.50 (17.61-33.39) | .020 |
| IgG4 | 17 | 427.57 (295.82-559.32) | 19 | 426.80 (323.42-530.18) | .261 |
| IgM | 22 | 14.97 (9.49-20.45) | 22 | 14.30 (9.99-18.61) | .654 |
| Innate immunity (ng/L) [c] | | | | | |
| IFN-γ | 4 | 56.06 (−98.47-210.58) | 3 | 14.52 (−1.59-30.63) | .475 |
| IL-1β | 23 | 40.70 (−38.51-119.90) | 21 | 14.10 (−10.77-38.98) | .499 |
| IL-6 | 16 | 3.42 (0.82-6.01) | 15 | 1.64 (0.19-3.10) | .572 |
| IL-12 (p70) | 4 | 2.43 (−2.97-7.84) | 5 | 0.70 (0.07-1.33) | .500 |
| TNF-α | 8 | 14.25 (−11.44-39.93) | 13 | 4.03 (2.18-5.89) | .899 |
| Acquired immunity (ng/L) [c] | | | | | |
| IL-2 | 1 | 2.24 | 1 | 0.20 | |
| IL-4 | 6 | 0.76 (−0.47-2.00) | 4 | 0.49 (−0.05-1.03) | .210 |
| IL-10 | 5 | 2.39 (−1.24-6.02) | 8 | 0.90 (0.29-1.51) | .298 |
| IL-13 | 3 | 2.90 (−5.49-11.29) | 8 | 3.72 (−0.49-7.93) | .166 |
| IL-17 | 2 | 53.17 (−590.08-696.43) | 2 | 7.01 (−26.79-40.81) | |
| TGF-β$_2$ ($\times 10^3$) | 21 | 7.86 (4.60-11.13) | 22 | 8.23 (4.42-12.04) | .646 |
| Chemokines (ng/L) [c] | | | | | |
| GRO-α | 21 | 899.78 (419.07-1380.49) | 21 | 1936.48 (398.10-3473.98) | .185 |
| IL-8 | 23 | 134.40 (46.94-221.86) | 23 | 56.73 (31.66-81.81) | .067 |
| MCP-1 | 22 | 165.41 (45.78-285.05) | 22 | 98.97 (38.39-159.55) | .288 |
| MIP-1β | 23 | 54.49 (−16.49-125.48) | 22 | 25.61 (13.90-37.31) | .405 |
| Growth factors (ng/L) [c] | | | | | |
| EGF ($\times 10^3$) | 23 | 24.14 (21.15-27.13) | 23 | 26.86 (23.57-30.15) | .061 |
| G-CSF | 3 | 10.14 (−8.14-28.42) | 5 | 12.85 (−1.89-27.60) | 1.000 |

TABLE 5-continued

Concentrations of immunoglobulins and cytokines in milk

|  | Initial (day 0) | | Final (day 21) | | |
| --- | --- | --- | --- | --- | --- |
|  | n | mean (95% CI [b]) | n | mean (95% CI [b]) | P [a] |
| GM-CSF | 15 | 22.73 (8.55-36.91) | 13 | 26.58 (6.92-46.23) | .347 |
| IL-5 | 3 | 3.57 (−4.35-11.49) | 0 | — | |
| IL-7 | 20 | 1.23 (0.79-1.68) | 16 | 12.61 (0.10-25.12) | .070 |

[a] paired t-test;
[b] 95% confidence interval;
[c] Abbreviations: EGF = epithelial growth factor; G-CSF = granulocyte colony stimulating factor; GM-CSF = granulocyte-macrophage colony stimulating factor; GRO-α = growth related oncogene-α; Ig = immunoglobulin; IL = interleukin; IFN-γ = interferon-γ; MCP-1 = monocyte chemoattractant protein; MIP-1β = macrophage inflammatory protein-1β; TGF-β$_2$ = transforming growth factor-β$_2$; TNF-α = tumor necrosis factor-α.

Blood Analyses:

The analyses of the blood samples are summarized in Tables 6 and 7. Three of the four Lewis antigen A/B phenotypes were detected among the participants but none of them showed the A+/B+ phenotype (data not shown). Generally, values obtained for the tested hematological and biochemical parameters were within physiological ranges at both sampling times. A significant decrease in the lymphocyte proportion (P=0.004) and an increase in that of PMN cells (P=0.011) after the probiotic treatment was noted (Table 6). Interestingly, major changes were detected in the blood lipid profile of the participants since triglycerides (P=0.012) as well as total (P=0.003), LDL (P=0.006) and VLDL (P=0.010) cholesterol levels in blood samples were significantly lower after the probiotic treatment (data not shown). No substantial changes were observed in the FAs detected in the cellular fraction of blood, except in adrenic acid (C22:4 n6) that was slightly lower (P=0.047) (data not shown).

The analysis of markers of oxidative stress showed a slight reduction of most of them after the probiotic intervention, although only the reduction in advanced oxidation protein products (AOPPs), when expressed both in terms of absolute concentration and after normalization for protein content, was statistically significant (P=0.008 and P=0.003, respectively; Table 6). The correlation analysis between oxidative stress parameters showed that after the probiotic intervention AOPPs were positively correlated with thiobarbituric acid-reactive material (TBARM, r=0.346, P=0.004) and nitrite levels (r=0.400; P=0.001) and negatively with isoprostanes (r=−0.254; P=0.035). Negative correlations between SH groups and TBARM (r=−0.427; P=0.000) and between isoprostanes and nitrite (r=−0.318; P=0.008) were also noted.

Blood levels of the different immunological compounds were also within their physiological ranges (Table 7). All the Igs were present in all the blood samples with the exception of IgE, which was not detected in two samples collected at day 21. IL-4, IFN-γ, TNF-α and all the chemokines were detected in more than 87% of the samples; IL-6, IL-12(p70), IL-7 and G-CSF were detected in 52-74% and the rest of these compounds could be measured in less than 50% of them. Decreased concentrations of IgA (P=0.047), IgG1 (P=0.066), IL-2 (P=0.098) and MCP-1 (P=0.062) were noted in blood samples after the probiotic treatment (Table 7).

TABLE 6

Blood hematological and biochemical parameters

|  | Initial (day 0) mean (95% CI [b]) | Final (day 21) mean (95% CI [b]) | P [a] |
| --- | --- | --- | --- |
| Hematological parameters [c] | | | |
| Leukocytes (10$^3$ cells/μL) | 6.33 (5.74-6.92) | 6.63 (5.93-7.33) | .293 |
| Red cells (10$^6$ cells/μL) | 4.61 (4.45-4.76) | 4.62 (4.51-4.72) | .883 |
| Hemoglobin (g/dL) | 13.00 (12.56-13.44) | 13.05 (12.69-13.41) | .730 |
| Hematocrit (%) | 40.16 (38.94-41.38) | 40.10 (39.08-41.13) | .901 |
| MCV (fL) | 87.35 (84.77-89.93) | 87.03 (84.46-89.60) | .548 |
| MCH (pg) | 28.29 (27.25-29.33) | 28.32 (27.45-29.18) | .883 |
| MCHC (g/dL) | 32.38 (31.78-32.97) | 32.56 (31.93-33.18) | .606 |
| RDW (%) | 14.43 (13.85-15.01) | 14.55 (14.01-15.09) | .419 |
| Platelets (10$^5$ cells/μL) | 2.69 (2.42-2.96) | 2.57 (2.34-2.80) | .260 |
| MPV (fL) | 8.32 (7.82-8.81) | 8.28 (7.79-8.76) | .863 |
| Lymphocytes (%) | 34.45 (31.51-37.38) | 31.06 (28.23-33.89) | .004 |
| Monocytes (%) | 5.22 (4.64-5.80) | 5.04 (4.49-5.59) | .367 |
| PMN (%) | 55.64 (52.20-59.08) | 58.85 (55.37-62.32) | .011 |
| Eosinophils (%) | 4.11 (2.47-5.76) | 4.06 (1.76-6.35) | .923 |
| Basophils (%) | 0.57 (0.45-0.69) | 0.53 (0.42-0.64) | .297 |
| Oxidative stress and nitric oxide metabolism parameters [c] | | | |
| AOPPs (μmol/L) | 60.81 (55.85-65.77) | 52.52 (47.39-57.66) | .003 |
| AOPPs (nmol/mg pr.) | 0.78 (0.72-0.84) | 0.68 (0.61-0.75) | .008 |
| SH groups (μmol/L) | 428.00 (412.00-444.00) | 422.00 (405.00-440.00) | .430 |
| SH groups (nmol/mg pr.) | 5.60 (5.19-6.00) | 5.48 (5.10-5.85) | .499 |
| TBARM (μmol/L) [d] | 24.40 (22.80-29.60) | 23.80 (22.40-30.80) | .697 |
| MDA (μmol/L) | 2.02 (1.76-2.28) | 2.02 (1.69-2.35) | .983 |

TABLE 6-continued

Blood hematological and biochemical parameters

| | Initial (day 0) mean (95% CI [b]) | Final (day 21) mean (95% CI [b]) | P [a] |
|---|---|---|---|
| 8-iso PG F$_{2\alpha}$ (pg/mL) | 180.00 (155.00-206.00) | 166.00 (142.00-190.00) | .175 |
| NOx (µmol/L) [d] | 22.14 (18.88-28.65) | 26.04 (17.58-34.51) | .438 |
| Nitrite (µmol/L) | 2.00 (1.72-2.27) | 1.99 (1.70-2.28) | .970 |
| Nitrate (µmol/L) [d] | 19.71 (15.89-27.11) | 23.21 (15.40-33.21) | .386 |

[a] Paired t-test
[b] 95% confidence interval for normally distributed data and Wilcoxon signed rank test when not 1;
[c] Abbreviations: MCH = mean corpuscular hemoglobin; MCHC = mean corpuscular hemoglobin concentration; MCV = mean corpuscular volume; MPV = mean platelet volume; PMN = polymorphonuclear cells; RDW = red blood cell distribution width; AOPPs = advanced oxidation protein products; TBARM = thiobarbituric acid-reactive material; MDA = malondialdehyde; NOx = nitric oxide metabolism end products; PG = prostaglandin; pr. = protein; SH = sulfhydryl
[d] No normal distribution.

TABLE 7

Concentrations of immunoglobulins and cytokines in blood

| | Initial (day 0) | | Final (day 21) | | |
|---|---|---|---|---|---|
| | n | mean (95% CI [b]) | n | mean (95% CI [b]) | P [a] |
| Immunoglobulins (g/L) [c] | | | | | |
| IgA | 23 | 2.51 (1.83-3.19) | 23 | 1.96 (1.72-2.20) | .047 |
| IgE (×10$^3$) | 23 | 0.82 (0.58-1.07) | 21 | 0.88 (0.58-1.18) | .486 |
| IgG1 | 23 | 10.18 (8.70-11.67) | 23 | 9.15 (8.11-10.19) | .066 |
| IgG2 | 23 | 5.12 (3.83-6.41) | 23 | 4.63 (3.77-5.48) | .259 |
| IgG3 | 23 | 1.12 (0.87-1.38) | 23 | 1.03 (0.79-1.27) | .191 |
| IgG4 | 23 | 0.44 (0.24-0.65) | 23 | 0.41 (0.23-0.59) | .353 |
| IgM | 23 | 0.90 (0.40-1.39) | 23 | 0.70 (0.46-0.94) | .144 |
| Innate immunity (ng/L) [c] | | | | | |
| IFN-γ | 21 | 125.99 (79.50-172.47) | 20 | 127.08 (92.18-161.97) | .588 |
| IL-1β | 11 | 6.44 (−5.46-18.34) | 10 | 6.36 (−5.27-17.99) | .411 |
| IL-6 | 13 | 7.75 (5.08-10.42) | 15 | 7.65 (4.91-10.38) | .292 |
| IL-12 (p70) | 14 | 586.52 (−661.38-1834.43) | 13 | 370.19 (−416.88-1157.26) | .336 |
| TNF-α | 22 | 21.06 (12.54-29.58) | 22 | 20.09 (13.13-27.06) | .799 |
| Acquired immunity (ng/L) [c] | | | | | |
| IL-2 | 7 | 4.48 (2.26-6.70) | 8 | 2.59 (0.59-4.59) | .098 |
| IL-4 | 20 | 2.93 (1.78-4.08) | 20 | 3.35 (2.31-4.39) | .196 |
| IL-10 | 4 | 20.10 (−35.19-75.39) | 3 | 23.63 (−67.56-114.81) | .685 |
| IL-13 | 2 | 317.00 (−3640.47-4274.47) | 2 | 287.09 (−3280.43-3854.61) | .508 |
| IL-17 | 9 | 37.73 (5.69-69.77) | 13 | 29.40 (4.59-54.21) | .906 |
| Chemokines (ng/L) [c] | | | | | |
| IL-8 | 21 | 9.09 (5.96-12.21) | 19 | 10.35 (7.07-13.62) | .818 |
| MCP-1 | 23 | 57.36 (45.19-69.53) | 23 | 52.52 (39.88-65.16) | .062 |
| MIP-1β | 23 | 75.24 (65.57-84.90) | 23 | 74.12 (64.55-83.69) | .691 |
| Growth factors (ng/L) [c] | | | | | |
| G-CSF | 17 | 49.85 (32.25-67.46) | 15 | 45.43 (35.42-55.44) | .650 |
| GM-CSF | 6 | 2.86 (−32.66-38.37) | 5 | 190.10 (−321.27-701.47) | .344 |
| IL-5 | 7 | 6.50 (1.54-11.46) | 7 | 5.90 (−2.53-14.34) | .752 |
| IL-7 | 12 | 30.73 (22.57-38.89) | 13 | 30.95 (22.18-39.73) | .424 |

[a] paired t-test;
[b] 95% confidence interval;
[c] Abbreviations: G-CSF = granulocyte colony stimulating factor; GM-CSF = granulocyte-macrophage colony stimulating factor; Ig = immunoglobulin; IL = interleukin; IFN-γ = interferon-γ; MCP-1 = monocyte chemoattractant protein; MIP-1β = macrophage inflammatory protein-1β; TNF-α = tumor necrosis factor-α.

Urine Analyses:

Values obtained for urine parameters were within physiological ranges and no differences associated to the probiotic treatment were observed (data not shown).

Conclusions:

L. salivarius PS2 was found effective in improving the total bacterial count in human milk, and a direct relationship between the decrease in staphylococcal and streptococcal counts and the clinical outcome was observed. Women recruited in this study reported a complete or notable improvement after the treatment. These results are indicative of the capability of L. salivarius PS2 to treat mastitis.

The administration of the probiotic did not affect the macronutrient content of breast milk, which was within normal ranges during the study. Electrolytes present in milk reflect the mammary epithelial integrity, which is achieved gradually after parturition through the closure of the tight junctions, and are controlled by transport mechanisms [Neville et al., Am. J. Clin. Nutr. 1991, 54, 81-92]. Reduced potassium levels and increased IgG3 levels after the L. salivarius PS2 treatment suggest a benefit for the epithelial integrity of the mammary gland. IgG1 and IgG3 transport is a competitive mechanism mediated by a receptor that favors the IgG3 subclass in milk, which have higher effector capabilities [Stapleton et al., *Nature Commun.* 2011, 2, 599] and reduces infection rate in immunodeficient individuals [Shapiro, *Immunotherapy* 2012, 4, 1835-9].

The levels of IL-8 and other cytokines and chemokines (such as IFN-γ, IL-1β, IL-6, IL-12(p'70), TNF-α, MCP-1 and MIP-1β) were reduced in milk as a consequence of the probiotic treatment, which may be responsible for the improvement of the inflammation state associated to mastitis. The 95% confidence intervals of different parameters were notably narrower after the probiotic treatment which indicates less dispersion of data and suggests more normalized levels.

The increase in the trophic factors EGF and TGF-$\beta_2$ may have contributed to immunomodulation in the mammary epithelium, which may also benefit the infant. TGF-$\beta_2$ is a key mammary immunoregulatory factor, promoting local IgA production and inducing oral tolerance mechanisms in infants [Stavnezer, *J. Immunol.* 1995, 155, 1647-1651; Oddy and Rosales, *Pediatr. Allergy Immunol.* 2010, 21, 47-59]. In contrast, oral supplementation with a *L. reuteri* strain to pregnant women reduced the TGF-$\beta_2$ levels in colostrum [Böttcher et al., *Pediatr. Allergy Immunol.* 2008, 19, 497-504]. This apparent contradictory result is indicative of differential immune responses exerted by different bacterial strains, and may explain why different probiotic strains have different applications.

Example 5: Liquid Composition 100 mL of a liquid milk-based composition packed in a 100 mL bottle comprising 8.1 g transgalacto-oligosaccharide, 0.9 g fructopolysaccharide, 750 μL fish oil and $10^8$ to $10^{10}$ colony forming units (cfu) of the *Lactobacillus salivarius* strain of the present invention, optionally also containing micronutrients recommended for lactation (e.g. folic acid, vitamin B1, vitamin B2, vitamin B6, vitamin B12, choline, vitamin C, calcium, iodine, zinc and iron), wherein the composition includes instructions to add the contents of the stick or stickpack of sachet to a beverage or food, to be consumed once or twice daily in order to prevent and/or treat mastitis or mastitis symptoms.

Example 6: Supplement

A stick or stickpack or a sachet comprising $10^8$ to $10^{10}$ colony forming units (cfu) of the *Lactobacillus salivarius* strain of the present invention, with instructions to add the contents of the stick or stickpack of sachet to a beverage or food, to be consumed once or twice daily in order to prevent and/or treat mastitis or mastitis symptoms. Suitably the beverage is a cold beverage or a warm beverage.

Example 7: Cereal Bar

A cereal bar comprising cereals (e.g. oats, wheat, corn, rice), suitably including cereals in the form of flakes, extruded cereals, etc, and the *Lactobacillus salivarius* strain according to the present invention in the range of $10^8$-$10^{10}$ colony forming units (cfu), and optionally also containing:
- fruits (e.g. cranberry, raisins, blackberry, blackcurrant, cherry, raspberry, strawberry, etc), suitably including dried or freeze dried fruits;
- seeds and/or nuts;
- syrups and/or oils;
- prebiotics (e.g. transgalacto-oligosaccharide, fructopolysaccharide);
- micronutrients recommended for lactation (e.g. folic acid, vitamin B1, vitamin B2, vitamin B6, vitamin B12, choline, vitamin C, calcium, iodine, zinc and iron).

The cereal bar may include instructions that the cereal bar is to be consumed once or twice daily in order to prevent and/or treat mastitis or mastitis symptoms.

The invention claimed is:

1. A freeze-dried strain of *Lactobacillus salivarius* having accession number LMG P-27027.

2. A composition comprising a freeze-dried strain of *Lactobacillus salivarius* having accession number LMG P-27027 and a physiologically acceptable carrier or excipient.

3. The composition according to claim 2, comprising $10^8$ to $10^{10}$ cfu of *Lactobacillus salivarius* per gram dry weight.

4. The composition according to claim 2, further comprising at least one ingredient selected from the group of non-digestible oligosaccharides, LC-PUFAs, further probiotics and micronutrients.

5. A composition comprising $10^5$ to $10^{11}$ cfu of freeze-dried *Lactobacillus salivarius* having accession number LMG P-27027 per gram dry weight of the composition, and a physiologically acceptable carrier or excipient.

6. A method of treatment of inflammation and/or infection of breast or udder tissue in a mammal, comprising administering to the mammal a composition comprising a freeze-dried strain of *Lactobacillus salivarius* having accession number LMG P-27027.

7. The method according to claim 6, for the treatment and/or prevention of mastitis in a human female.

8. The method according to claim 6, wherein the strain of *Lactobacillus salivarius* is administered more than once per day in a dose of $10^8$ to $10^{10}$ colony forming units (cfu) per dose.

9. The method according to claim 8, wherein the strain of *Lactobacillus salivarius* is administered three times per day in a dose of $10^8$ to $10^{10}$ colony forming units (cfu) per dose.

10. The method according to claim 6, wherein the composition further comprises at least one ingredient selected from the group consisting of non-digestible oligosaccharides, LC-PUFAs, further probiotics and micronutrients.

* * * * *